(12) United States Patent
Tao et al.

(10) Patent No.: US 6,933,376 B2
(45) Date of Patent: Aug. 23, 2005

(54) CELL CYCLE POLYNUCLEOTIDES, POLYPEPTIDES AND USES THEREOF

(75) Inventors: Yumin Tao, Ames, IA (US); William J. Gordon-Kamm, Urbandale, IA (US); Keith S. Lowe, Johnston, IA (US); Matthew A. Bailey, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 205 days.

(21) Appl. No.: 09/496,444

(22) Filed: Feb. 2, 2000

(65) Prior Publication Data

US 2003/0041343 A1 Feb. 27, 2003

Related U.S. Application Data

(63) Continuation-in-part of application No. 09/398,858, filed on Sep. 20, 1999, which is a continuation-in-part of application No. 09/257,131, filed on Feb. 25, 1999.
(60) Provisional application No. 60/101,551, filed on Sep. 23, 1998, and provisional application No. 60/119,857, filed on Feb. 12, 1999.

(51) Int. Cl.$^7$ .............................................. C12N 15/29
(52) U.S. Cl. ..................................................... 536/23.6
(58) Field of Search ............................ 536/23.6, 23.1; 435/320.1, 419, 252.3, 468; 800/290, 298

(56) References Cited

U.S. PATENT DOCUMENTS 6,165,753 A   12/2000 Coats et al.

OTHER PUBLICATIONS

Ishida et al. High efficiency transformation of maize (Zea mays L.) mediated by Agrobacterium tumefaciens. Nature Biotechnology, Jun. 1996, vol. 14, pp. 745–750.*
Sgambato et al. Overexpression of cyclin E in the HC11 mouse mammary epithelial cell line is asociated with growth inhibition and increased expression of p27kip1. Cancer Research. 1996, vol. 56, pp. 1389–1399.*
Reed, S.I. Control of the G1/S transition. Cancer Surveys. 1997, vol. 29, pp. 7–23.*
Kende et al, Genbank Accession X82035, Nov. 1996.*
Doerks et al, "Protein annotation: detective work for function prediction", Jun. 1998, Trends in Genetics, vol. 14, No. 6, pp. 248–250.*
Hemerly et al, "Dominant negative mutants of the Cdc2 kinase uncouple cell division from iterative plant development", 1995, The Embo Journal, vol. 14, No. 16, pp. 3925–3936.*
Dahl et al., "The D–Type Alfalfa Cyclin Gene cycMS4 Complements $G_1$ Cyclin–Deficient Yeast and Is Induced in the $G_1$ Phase of the Cell Cycle", *Plant Cell* 7:1847–1857 (1995).
Lew et al., "Isolation of Three Novel Human Cyclins by Rescue of $G_1$ Cyclin (Cln) Function in Yeast", *Cell* 66:1197–1206 (1991).
Pines, J., "Cyclins and cyclin–dependent kinases: take your partners", *Trends. Biochem. Sci.* 18:195–197 (1993).
Renaudin et al., "Plant cyclins: a unified nomenclature for plant A–, B– and D–type cyclins based on sequence organization", *Plant. Mol. Biol.* 32:1003–1018 (1996).
Won et al., "Activation of cyclin E/CDK2 is coupled to site–specific autophosphorylation and ubiquitin–dependent degradation of cyclin E", *The EMBO Journal* 15:4182–4193 (1996).
Adam et al., "Retinoblastoma Protein Contains a C–terminal Motif That Targets It for Phosphorylation by Cyclin–cdk Complexes", *Mol. Cell. Biol.* 19(2):1068–1080 (1999).
Gudas et al., "Cyclin E2, a Novel $G_1$ Cyclin That Binds Cdk2 and Is Aberrantly Expressed in Human Cancers", *Mol. Cell. Biol.* 19:612–622 (1999).
Harbour et al., "Cdk Phosphorylation Triggers Sequential Intramolecular Interactions that Progressively Block Rb Functions as Cells Move through G1", *Cell* 98:859–869 (1999).
Lundberg et al., "Functional Inactivation of the Retinoblastoma Protein Requires Sequential Modification by at Least Two Distinct Cyclin–cdk Complexes", *Mol. Cell. Biol.* 18(2):753–761 (1998).

* cited by examiner

*Primary Examiner*—Elizabeth F. McElwain
*Assistant Examiner*—Cynthia Collins
(74) *Attorney, Agent, or Firm*—Pioneer Hi-Bred International, Inc.

(57) ABSTRACT

The invention provides isolated polynucleotides and their encoded proteins that are involved in cell cycle regulation. The invention further provides vectors, recombinant expression cassettes, host cells, transgenic plants, and antibody compositions. The present invention provides methods and compositions relating to altering cell cycle protein content and/or composition of plants.

4 Claims, No Drawings

SEQUENCE LISTING

<160> NUMBER OF SEQ ID NOS: 8

<210> SEQ ID NO 1
<211> LENGTH: 1636
<212> TYPE: DNA
<213> ORGANISM: Zea mays
<220> FEATURE:
<221> NAME/KEY: CDS
<222> LOCATION: (109)...(1381)
<221> NAME/KEY: misc_feature
<222> LOCATION: (1)...(1636)
<223> OTHER INFORMATION: n = A,T,C or G

<400> SEQUENCE: 1

```
tcacggggct cctccgtccg taaggcaccg ccgcagcgtc tcggctggat caacaggccg        60
gccgatccgt cttcttcccc tcctcctgcg ggtcggcgtt tggggatc atg gcg gcg       117
                                                     Met Ala Ala
                                                       1 cgg gcg gct gac gag aac agg aga ccg gcg gca ggg aag ccc gcg cca       165
Arg Ala Ala Asp Glu Asn Arg Arg Pro Ala Ala Gly Lys Pro Ala Pro
      5                  10                  15 ggc gtc cga gac atg gcg agc cgg cgc gcg ctc acg gac atc aag aac       213
Gly Val Arg Asp Met Ala Ser Arg Arg Ala Leu Thr Asp Ile Lys Asn
 20                  25                  30                  35 ctc gtc ggg gct gcc ccg tac ccc tac gcc gtc gcc aag aag ccc atg       261
Leu Val Gly Ala Ala Pro Tyr Pro Tyr Ala Val Ala Lys Lys Pro Met
              40                  45                  50
```

```
                                                        -continued ctg cag aag agc aaa agg gac gaa aag cag cca gcg ttg gca agc agc    309
Leu Gln Lys Ser Lys Arg Asp Glu Lys Gln Pro Ala Leu Ala Ser Ser
             55                  60                  65 cgg ccc atg aca agg aaa ttc gcc gcc tcc ttg gcg agc aag ggc caa    357
Arg Pro Met Thr Arg Lys Phe Ala Ala Ser Leu Ala Ser Lys Gly Gln
         70                  75                  80 cct gaa tgt cag ccg atc gta gct gat cca gaa ccc gaa gtt tgt caa    405
Pro Glu Cys Gln Pro Ile Val Ala Asp Pro Glu Pro Glu Val Cys Gln
     85                  90                  95 cag aag gaa tca gta ggc gat ggc acc gtt gat att gac gtg gaa ctc    453
Gln Lys Glu Ser Val Gly Asp Gly Thr Val Asp Ile Asp Val Glu Leu
100                 105                 110                 115 tac gag ctg gtc gac ggt agt gat agt gac atc gac atg ggt gcg aca    501
Tyr Glu Leu Val Asp Gly Ser Asp Ser Asp Ile Asp Met Gly Ala Thr
                120                 125                 130 gag aac aag gac att atg aac gaa gat gaa ttg ctc atg gat att gac    549
Glu Asn Lys Asp Ile Met Asn Glu Asp Glu Leu Leu Met Asp Ile Asp
            135                 140                 145 agt gca gac tcg ggg aac ccg ctt gct gca aca gaa tat gtt aaa gag    597
Ser Ala Asp Ser Gly Asn Pro Leu Ala Ala Thr Glu Tyr Val Lys Glu
        150                 155                 160 ctt tac acc ttt tac aga gaa aat gag gct aag agt tgt gta agg cca    645
Leu Tyr Thr Phe Tyr Arg Glu Asn Glu Ala Lys Ser Cys Val Arg Pro
    165                 170                 175 gat tac atg tcc agc caa caa gac ata aac tca aag atg aga gca att    693
Asp Tyr Met Ser Ser Gln Gln Asp Ile Asn Ser Lys Met Arg Ala Ile
180                 185                 190                 195 ctg att gac tgg ctg att gag gtt cac tac aag ttt gaa ctg atg gat    741
Leu Ile Asp Trp Leu Ile Glu Val His Tyr Lys Phe Glu Leu Met Asp
                200                 205                 210 gag acg ctc ttt ctt atg gta aac ata ata gat aga ttc ttg gaa aag    789
Glu Thr Leu Phe Leu Met Val Asn Ile Ile Asp Arg Phe Leu Glu Lys
            215                 220                 225 gaa gtg gtt cca agg aag aag cta caa ctg gtt gga gtc aca gct atg    837
Glu Val Val Pro Arg Lys Lys Leu Gln Leu Val Gly Val Thr Ala Met
        230                 235                 240 ctc ctc gct tgt aaa tat gag gag gta tct gtt cca gtt gtt gag gac    885
Leu Leu Ala Cys Lys Tyr Glu Glu Val Ser Val Pro Val Val Glu Asp
    245                 250                 255 ctt gtg ctg ata tct gac cgt gcc tac aca aaa ggg caa att tta gaa    933
Leu Val Leu Ile Ser Asp Arg Ala Tyr Thr Lys Gly Gln Ile Leu Glu
260                 265                 270                 275 atg gaa aag ttg att ctg aac acg ctg cag ttc aac atg tct gtt cca    981
Met Glu Lys Leu Ile Leu Asn Thr Leu Gln Phe Asn Met Ser Val Pro
                280                 285                 290 aca cct tat gtc ttc atg aag agg ttt ctg aaa gct gca gat gca gat   1029
Thr Pro Tyr Val Phe Met Lys Arg Phe Leu Lys Ala Ala Asp Ala Asp
            295                 300                 305 aaa cag ctt gag cta gcg tca ttt ttc atg ctg gag ctc tgc ttg gta   1077
Lys Gln Leu Glu Leu Ala Ser Phe Phe Met Leu Glu Leu Cys Leu Val
        310                 315                 320 gaa tac caa atg ctg aat tat cgg cct tcg cat ctg gct gct gct gcg   1125
Glu Tyr Gln Met Leu Asn Tyr Arg Pro Ser His Leu Ala Ala Ala Ala
    325                 330                 335 gtt tat act gca cag tgt gct atc aat cgt tgc cag cac tgg aca aag   1173
Val Tyr Thr Ala Gln Cys Ala Ile Asn Arg Cys Gln His Trp Thr Lys
340                 345                 350                 355 gtc tgc gag tct cat agc aga tac act agc gac caa ctc ctg gag tgc   1221
Val Cys Glu Ser His Ser Arg Tyr Thr Ser Asp Gln Leu Leu Glu Cys
                360                 365                 370
```

```
tcg agg atg atg gta gat ttt cac cag aag gct gga acc agt aag ctc    1269
Ser Arg Met Met Val Asp Phe His Gln Lys Ala Gly Thr Ser Lys Leu
        375                 380                 385 act ggc gtg cac agg aag tac agt acc tac aag ttc ggt tgc gtg gcc    1317
Thr Gly Val His Arg Lys Tyr Ser Thr Tyr Lys Phe Gly Cys Val Ala
        390                 395                 400 aag att ttg cct gcg cag ttc ctg ctg gag tcg gga ggg aca ccg cct    1365
Lys Ile Leu Pro Ala Gln Phe Leu Leu Glu Ser Gly Gly Thr Pro Pro
        405                 410                 415 cct tca ggt gca aac t agttgaatcg acctattcaa ctgggtggat tttttaaagt  1421
Pro Ser Gly Ala Asn
420 ttttagaata ctccatgaac aagatgcaga aaacatcgtg ttgatgttgc ccaaaagtgc  1481 atcgaatttc tttggagagt tatgattaac aactttttt ttatctatgt tgaatgacga   1541 gtgacggtcg gtcacgttgt gcttgtgcag ttatactgcg gctaataaca aactgtccag  1601 ttnttctnaa aaaaaaaaaa aaaaaaaaaa aaaaa                             1636
```

<210> SEQ ID NO 2
<211> LENGTH: 424
<212> TYPE: PRT
<213> ORGANISM: Zea mays

<400> SEQUENCE: 2

```
Met Ala Ala Arg Ala Ala Asp Glu Asn Arg Arg Pro Ala Ala Gly Lys
1               5                   10                  15

Pro Ala Pro Gly Val Arg Asp Met Ala Ser Arg Arg Ala Leu Thr Asp
            20                  25                  30

Ile Lys Asn Leu Val Gly Ala Ala Pro Tyr Pro Tyr Ala Val Ala Lys
        35                  40                  45

Lys Pro Met Leu Gln Lys Ser Lys Arg Asp Glu Lys Gln Pro Ala Leu
    50                  55                  60

Ala Ser Ser Arg Pro Met Thr Arg Lys Phe Ala Ala Ser Leu Ala Ser
65                  70                  75                  80

Lys Gly Gln Pro Glu Cys Gln Pro Ile Val Ala Asp Pro Glu Pro Glu
                85                  90                  95

Val Cys Gln Gln Lys Glu Ser Val Gly Asp Gly Thr Val Asp Ile Asp
            100                 105                 110

Val Glu Leu Tyr Glu Leu Val Asp Gly Ser Asp Ser Asp Ile Asp Met
        115                 120                 125

Gly Ala Thr Glu Asn Lys Asp Ile Met Asn Glu Asp Glu Leu Leu Met
    130                 135                 140

Asp Ile Asp Ser Ala Asp Ser Gly Asn Pro Leu Ala Ala Thr Glu Tyr
145                 150                 155                 160

Val Lys Glu Leu Tyr Thr Phe Tyr Arg Glu Asn Glu Ala Lys Ser Cys
                165                 170                 175

Val Arg Pro Asp Tyr Met Ser Ser Gln Gln Asp Ile Asn Ser Lys Met
            180                 185                 190

Arg Ala Ile Leu Ile Asp Trp Leu Ile Glu Val His Tyr Lys Phe Glu
        195                 200                 205

Leu Met Asp Glu Thr Leu Phe Leu Met Val Asn Ile Ile Asp Arg Phe
    210                 215                 220

Leu Glu Lys Glu Val Val Pro Arg Lys Lys Leu Gln Leu Val Gly Val
225                 230                 235                 240

Thr Ala Met Leu Leu Ala Cys Lys Tyr Glu Glu Val Ser Val Pro Val
                245                 250                 255
```

-continued

```
Val Glu Asp Leu Val Leu Ile Ser Asp Arg Ala Tyr Thr Lys Gly Gln
            260                 265                 270
Ile Leu Glu Met Glu Lys Leu Ile Leu Asn Thr Leu Gln Phe Asn Met
        275                 280                 285
Ser Val Pro Thr Pro Tyr Val Phe Met Lys Arg Phe Leu Lys Ala Ala
    290                 295                 300
Asp Ala Asp Lys Gln Leu Glu Leu Ala Ser Phe Phe Met Leu Glu Leu
305                 310                 315                 320
Cys Leu Val Glu Tyr Gln Met Leu Asn Tyr Arg Pro Ser His Leu Ala
                325                 330                 335
Ala Ala Ala Val Tyr Thr Ala Gln Cys Ala Ile Asn Arg Cys Gln His
            340                 345                 350
Trp Thr Lys Val Cys Glu Ser His Ser Arg Tyr Thr Ser Asp Gln Leu
        355                 360                 365
Leu Glu Cys Ser Arg Met Met Val Asp Phe His Gln Lys Ala Gly Thr
    370                 375                 380
Ser Lys Leu Thr Gly Val His Arg Lys Tyr Ser Thr Tyr Lys Phe Gly
385                 390                 395                 400
Cys Val Ala Lys Ile Leu Pro Ala Gln Phe Leu Leu Glu Ser Gly Gly
                405                 410                 415
Thr Pro Pro Ser Gly Ala Asn
            420
```

<210> SEQ ID NO 3
<211> LENGTH: 21
<212> TYPE: DNA
<213> ORGANISM: Artificial Sequence
<220> FEATURE:
<221> NAME/KEY: primer_bind
<222> LOCATION: (1)...(21)

<400> SEQUENCE: 3
ctagtttgca cctgaaggag g     21

<210> SEQ ID NO 4
<211> LENGTH: 22
<212> TYPE: DNA
<213> ORGANISM: Artificial Sequence
<220> FEATURE:
<221> NAME/KEY: primer_bind
<222> LOCATION: (1)...(22)

<400> SEQUENCE: 4
gctaagagtt gtgtaaggcc ag     22

<210> SEQ ID NO 5
<211> LENGTH: 21
<212> TYPE: DNA
<213> ORGANISM: Artificial Sequence
<220> FEATURE:
<221> NAME/KEY: primer_bind
<222> LOCATION: (1)...(21)

<400> SEQUENCE: 5
ttgggcaaca tcaacacgat g     21

<210> SEQ ID NO 6
<211> LENGTH: 23
<212> TYPE: DNA
<213> ORGANISM: Artificial Sequence

```
-continued

<220> FEATURE:
<221> NAME/KEY: primer_bind
<222> LOCATION: (1)...(23)

<400> SEQUENCE: 6
aacccgcttg ctgcaacaga ata                                              23

<210> SEQ ID NO 7
<211> LENGTH: 23
<212> TYPE: DNA
<213> ORGANISM: articifial organism
<220> FEATURE:
<221> NAME/KEY: primer_bind
<222> LOCATION: (1)...(23)

<400> SEQUENCE: 7
aatccaccca gttgaatagg tcg                                              23

<210> SEQ ID NO 8
<211> LENGTH: 23
<212> TYPE: DNA
<213> ORGANISM: Artificial Sequence
<220> FEATURE:
<221> NAME/KEY: primer_bind
<222> LOCATION: (1)...(23)

<400> SEQUENCE: 8
atccgtcttc ttcccctcct cct                                              23
```

CELL CYCLE POLYNUCLEOTIDES, POLYPEPTIDES AND USES THEREOF

This application claims priority to U.S. Ser. No. 60/119,857 filed Feb. 12, 1999, which is CIP of U.S. Ser. No. 09/398,858 filed Sep. 20, 1999 which was converted from U.S. Ser. No. 60/101,551 filed Sep. 23, 1998, and which is a CIP of U.S. Ser. No. 09/257,131 filed Feb. 25, 1999 the disclosures of which are incorporated herein by reference.

TECHNICAL FIELD

The present invention relates generally to plant molecular biology. More specifically, it relates to nucleic acids and methods for modulating their expression in plants.

BACKGROUND OF THE INVENTION

Cell division plays an important role during all phases of plant development. The continuation of organogenesis and growth responses to a changing environment requires precise spatial, temporal and developmental regulation of cell division activity in meristems (and in cells with the capability to form new meristems such as in lateral root formation). Such control of cell division is also important in organs themselves (i.e. separate from meristems per se), for example, in leaf expansion, secondary growth, and endoreduplication.

A complex network controls cell proliferation in eukaryotes. Regulatory pathways communicate environmental constraints, such as nutrient availability, mitogenic signals such as growth factors or hormones, or developmental cues such as the transition from vegetative to reproductive. Ultimately, these regulatory pathways control the timing, frequency (rate), plane and position of cell divisions.

The basic mechanism of cell cycle control is conserved among eukaryotes. A catalytic protein serine/threonine kinase and an activating cyclin subunit control progress through the cell cycle. The protein kinase is generally referred to as a cyclin-dependent-kinase (CDK), whose activity is modulated by phosphorylation and dephosphorylation events and by their association with regulatory subunits, called cyclins. CDKs require association with cyclins for activation, and the timing of activation is largely dependent upon cyclin expression. CDKs are a family of serine/threonine protein kinases that regulate individual cell cycle transitions.

Eukaryote genomes typically encode multiple cyclin and CDK genes. In higher eukaryotes, different members of the CDK family act in different stages of the cell cycle. Cyclin genes are classified according to sequence, the timing of their appearance or activity during the cell cycle, and the cell cycle regulatory proteins with which they interact. In addition to cyclin and CDK subunits, CDKs are often physically associated with other proteins that alter localization, substrate specificity, or activity. A few examples of such CDK interacting proteins are the CDK inhibitors, members of the Retinoblastoma-associated protein (Rb) family, and the Constitutive Kinase Subunit (CKS).

The protein kinase activity of the complex is regulated by feedback control at certain checkpoints. At such checkpoints the CDK activity becomes limiting for further progress. When the feedback control network senses the completion of a checkpoint, CDK is activated and the cell passes through to the next checkpoint. Changes in CDK activity are regulated at multiple levels, including reversible phosphorylation of the cell cycle factors, changes in subcellular localization of the complex, and the rates of synthesis and destruction of limiting components. P. W. Doerner, *Cell Cycle Regulation in Plants, Plant Physoil.*, 106:823–827 (1994).

Plants have unique developmental features that distinguish them from other eukaryotes. Plant cells do not migrate, and thus only cell division, expansion and programmed cell death determine morphogenesis. Organs are formed throughout the entire life span of the plant from specialized regions called meristems. In addition, many differentiated cells have the potential to both dedifferentiate and to reenter the cell cycle. There are also numerous examples of plant cell types that undergo endoreduplication, a process involving nuclear multiplication without cytokinesis. The study of plant cell cycle control genes is expected to contribute to the understanding of these unique phenomena. O. Shaul et al., *Regulation of Cell Division in Arabidopsis, Critical Reviews in Plant Sciences*, 15(2): 97–112 (1996).

Cell division in higher eukaryotes is controlled by two main checkpoints in the cell cycle that prevent the cell from entering either M- or S-phase of the cycle prematurely. Evidence from yeast and mammalian systems has shown that over-expression of key cell cycle activating genes can either trigger cell division in non-dividing cells, or stimulate division in previously dividing cells (i.e. the duration of the cell cycle is decreased and cell size is reduced). Examples of genes whose over-expression has been shown to stimulate cell division include cyclins (see, e.g. Doerner et al., *Nature* (1996) 380:520–423; Gudas et al., Mol. Cell. Biol. (1999) 19:612–622; Wang et al., *Nature* (1994) 369:669–671; Quelle et al., *Genes Dev.* (1993) 7:1559–1571, E2F transcription factors (see, e.g. Johnson et al., *Nature* (1993) 365:349–352; Lukas et al., (1996) *Mol. Cell. Biol.* 16:1047–1057), cdc25 (see, e.g. Bell et al., (1993) Plant Molecular Biology 23:445–451; Draetta et al., (1996) *BBA* 1332:53–63), and mdm2 (see, e.g. Teoh et al., (1997) *Blood* 90:1982–1992). Conversely, other gene products have been found to participate in negative regulation and/or checkpoint control, effectively blocking or retarding progression through the cell cycle. (see MacLachlan et al., (1995) *Critical Rev. Eukaroytic Gene Expression* 5(2):127–156).

Current methods for genetic engineering in agronomically important crops such as maize and soybean require a specific cell type as the recipient of new DNA. In maize, these cells are found in relatively undifferentiated, rapidly growing callus cells or on the scutellar surface of the immature embryo (which gives rise to callus). Irrespective of the delivery method currently used, DNA is introduced into literally thousands of cells, yet transformants are recovered at frequencies of $10^{-5}$ relative to transiently-expressing cells. In soybean, these cells are found in relatively undifferentiated, rapidly growing callus or suspension cells, or in nodal meristematic regions of the plant. Exacerbating this problem, the trauma that accompanies DNA introduction directs recipient cells into cell cycle arrest and accumulating evidence suggests that many of these cells are directed into apoptosis or programmed cell death. (Bowen et al., Tucson International Mol. Biol. Meetings). It would therefore be desirable to increase transformation efficiency.

Over the period between 1950 and 1980, the increase in maize production worldwide outpaced both wheat and rice. Despite a temporary downswing in the early to mid-1980's (due to both environmental and political factors) world maize production has risen steadily from around 145 million tons in 1950 to nearly 500 million tons by 1990. Increases in yield and harvested area have been the predominant contributors to enhanced world production; with yield playing the major role in industrialized countries and area expansion being most important in developing countries. Yet, over the next ten years it's also predicted that meeting the demand for corn worldwide will require an additional 20% over current production (Dowswell, C. R., Paliwal, R. L., Cantrell, R. P., 1996, Maize in the Third World, Westview Press, Boulder, Colo.).

The components most often associated with maize productivity are grain yield or whole-plant harvest for animal feed (in the forms of silage, fodder, or stover). Thus the relative growth of the vegetative or reproductive organs might be preferred, depending on the ultimate use of the crop. Whether the whole plant or the ear are harvested, overall yield will depend strongly on vigor and growth rate. In modern maize hybrids, the impact of heterosis on overall plant vigor and yield has been unarguably demonstrated (Duvick, D. N.,1984, In: Genetic contributions to yield gains in five major crop plants. W. R. Fehr, ed. CSSA, Madison, Wis.).

Corn breeders since the 1930's have been selectively breeding by identifying inbreds that in combination produce hybrid vigor well beyond either parent. Surprisingly little is known about why hybrids are so much larger than their parent inbreds, although there are some interesting observations in the literature. In metabolic studies, heterosis (increases over either parent) has been observed for physiological traits such as P uptake by roots (Baliger and Barber, 1979; Nielsen and Barber, 1978), but for many enzymatic traits the hybrid is often intermediate to the inbred parents (Hageman, R. H., Leng, E. R., Dudley, J. W. 1967. Adv. Agron. 19:45–86; Chevalier, P., Schrader, L. E. 1977. Crop Sci. 17:897–901; Schrader, L. E. 1974. Crop Sci. 14:201–205; Schrader, L. E. 1985. PP 79–89. In: Exploitation of physiological and genetic variability to enhance crop productivity. Harper, J. E. ed. Am. Soc. Plant Physiol. Rockville, Md., Schrader, L. E., Cataldo, D. A., Peterson, D. M., Vogelzang, R. D. 1974. Plant Physiol. 32:337–341).

Anatomical data is less confusing. In summarizing data from an earlier publication, Kiesselbach states that approximately 10% of the increased vigor of the hybrid over its inbred parents is due to cell enlargement, and 90% can be accounted for simply by increased cell numbers (Kiesselbach, T. A. 1922, 1949. The Structure and Reproduction of Corn, Nebraska Agric. Exp. Stn. Res. Bull. 161). Recently it was shown that overexpressing a B cyclin in Arabidopsis resulted in increased root biomass and the root cells were smaller (indicative of accelerated cell division), but the overall plant morphology was not perturbed (Doerner et al., 1996).

SUMMARY OF THE INVENTION

The invention provides isolated polynucleotides and their encoded proteins that are involved in cell cycle regulation. The invention further provides vectors, recombinant expression cassettes, host cells, transgenic plants, and antibody compositions. The present invention provides methods and compositions relating to altering cell cycle protein content and/or composition of plants.

Definitions

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "nucleic acid" means a polynucleotide and includes single or double-stranded polymer of deoxyribonucleotide or ribonucleotide bases. Nucleic acids may also include modified nucleotides that permit correct read through by a polymerase and do not alter the expression of a polypeptide encoded by the polynucleotide.

As used herein, "CycE polynucleotide" means a polynucleotide which encodes a polypeptide that i) binds to Cdk2 and Rb proteins, ii) contains a cyclin box (Jeffrey et al. 1995, Nature 367:313–320P, and iii) contains the conserved motif TTPXS near the carboxy-terminus.

As used herein, "polypeptide" means proteins, protein fragments, modified proteins, amino acid sequences and synthetic amino acid sequences. The polypeptide may be glycosylated or not.

As used herein, "plant" includes but is not limited to plant cells, plant tissue and plant seeds.

By "fragment" is intended a portion of the nucleotide sequence or a portion of the amino acid sequence and hence protein encoded thereby. Preferably fragments of a nucleotide sequence may encode protein fragments that retain the biological activity of the native nucleic acid. However, fragments of a nucleotide sequence which are useful as hybridization probes generally do not encode fragment proteins retaining biological activity. Fragments of a nucleotide sequence are generally greater than 10 nucleotides, preferably at least 20 nucleotides and up to the entire nucleotide sequence encoding the proteins of the invention. Generally probes are less than 1000 nucleotides and preferably less than 500 nucleotides. Fragments of the invention include antisense sequences used to decrease expression of the inventive nucleic acids. Such antisense fragments may vary in length ranging from at least about 20 nucleotides, about 50 nucleotides, about 100 nucleotides, up to and including the entire coding sequence.

By "variants" is intended substantially similar sequences. Generally, nucleic acid sequence variants of the invention will have at least 50%, 55%, 60, 65%, 70%, 75%, 80%, 85%, or preferably 90%, more preferably at least 95% and most preferably at least 98% sequence identity to the native nucleotide sequence. Generally, polypeptide sequence variants of the invention will have at least about 50%, 55%, 60%, 65%, 70%, 75% 80%, 85%, 90%, 95% or at least 98% sequence identity to the native protein.

As used herein, "sequence identity" in the context of two nucleic acid sequences includes reference to the residues in the two sequences that are the same when aligned for maximum correspondence over the entire coding sequence of the present polynucleotides. As used herein, sequence identity is determined using the GCG/bestfit program, GAP 10 using a gap creation penalty of 50 and a gap extension penalty of 3.

GAP uses the algorithm of Needleman and Wunsch (J. Mol. Biol. 48:443–453, 1970) to find the alignment of two complete sequences that maximizes the number of matches and minimizes the number of gaps. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater. The scoring matrix used in Version 10 of the Wisconsin Genetics Software Package is BLOSUM62 (see Henikoff & Henikoff (1989) *Proc. Natl. Acad. Sci. USA* 89:10915).

As used herein, "sequence similarity" or "sequence identity" in the context of two polypeptide sequences includes reference to the residues in the two sequences that are the same when aligned for maximum correspondence over the entire sequence of the present polypeptides. As used herein, sequence similarity is determined using the GCG/bestfit program, GAP 10 using a gap creation penalty of 8 and a gap extension penalty of 2.

Other methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237–244 (1988); Higgins and Sharp, *CABIOS* 5:151–153 (1989); Corpet et al., *Nucleic Acids Research* 16:10881–90 (1988); Huang et al., *Computer Applications in the Biosciences* 8:155–65 (1992), and Pearson et al., *Methods in Molecular Biology* 24:307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See *Current Protocols in Molecular Biology*, Chapter 19, Ausubel et al., Eds., Greene Publishing and Wiley-Interscience, New York (1995). Software for performing BLAST analyses is publicly available, e.g., through the National Center for Biotechnology Information (http://www.ncbi.nlm.nih.gov/). The BLAST algorithm performs a statistical analysis of the similarity between two sequences (see, e.g., Karlin & Altschul, *Proc. Nat'l. Acad. Sci. USA* 90:5873–5877 (1993)). One measure of similarity provided by the BLAST algorithm is the smallest sum probability (P(N)), which provides an indication of the probability by which a match between two nucleotide or amino acid sequences would occur by chance.

By "functionally equivalent" is intended that the sequence of the variant defines a chain that produces a protein having substantially the same biological effect as the native protein of interest. The variant is catalytically active.

By "modulate" is intended to increase, decrease, influence or change.

DETAILED DESCRIPTION OF THE INVENTION

As part of a complex with CDK2, Cyclin E (CycE) protein is an integral component required for phosphorylation of retinoblastoma. The phosphorylation of Rb results in the release of E2F, which then activates transcription of numerous genes involved in DNA replication. Thus CycE plays a significant role in the transition from G1 to S phase of the cell cycle. Similar to Cyclin-D (another G1-S phase stimulating protein) CycE genes from heterologous species have been found to complement Saccharomyces cerevisiae cells lacking the G1 cyclin function required for progression through START. CycE overexpression has been found to stimulate S-phase in various cell types in both *Drosophila* and mammalian cells (Ohtsubo, M., Roberts, J. M., 1993, Science 259:1908–1912; Wimmels, A., Lucibello, F. C., Sewing, A., Adolf, S, Muller, R., 994, Oncogene 9:995–997; Resnitzky, D. M. G., Bujard, H., Reed, S. I., 1994, Mol Cell Biol. 14:1669–1679; Ohtsubo, M., Theadoras, A. M., Schumacher, J., Roberts, J. M., Pagano, M., 1995, Mol Cell Biol. 15:2612–2624. Evidence across a variety of fauna including *Homo sapiens, Drosophila melanogaster, Xenopus laevis,* zebrafish and mice suggests that the role of CycE is similar across these genera; activity of this protein promotes cell cycle entry into S-phase and is involved in such processes as endocycling and organ pattern development.

Cells transformed to modulate the level of polypeptides that stimulate the transition of G1 to S phase will increase transformation frequencies compared to non-transformed plants. The transformation can be transient or stable, thus DNA, RNA, or proteins can be introduced into the cells. Proteins that influence the transition from the G1 to S phase include CycD, CycE, E2F, RepA, cdk2, cdk4, Rb, or CKI. If the cell is transformed with DNA, the DNA is operably linked to a promoter. In order to stimulate transition from the G1 to S phase levels of CycD, CycE, E2F, Geminiviral replication protein such as RepA, cdk2, or cdk4 protein are increased, levels of Rb or CKI are decreased.

The above polypeptides or polynucleotides can be introduced into host cells by known methods to enhance transformation efficiency. Sequences from various sources are known. For example Wheat Dwarf Virus Rep and RepA sequences are in GenBank Accession No. X82104 and MSV C1 Accession No. AJ012641; Tomato Golden Mosaic Virus replication proteins A11, A12, and A13 in GenBank Accession No. K02029 and Embo J. 3, 2197–2205 (1984) Hamilton, W. D. O. et al.; Beet Curly Top Virus replication protein in GenBank Accession No. X97203 and Dur. J. Plant Pathol., 104, 77–84 (1999) Briddon, R. W.; cdk2 Est from soybean in GenBank Accession No. AW279429; *Homo sapiens* cdk2 in GenBank Accession No. NM 001798 and Nature 353 (6340), 1174–177 (1991) Tsai, L. H. et al.; cdk4 in soybean in GenBank Accession No. AW 164283; *Homo sapiens* cdk4 in GenBank Accession No. NM 000075 and Cytogenet. Cell Genet 66(1), 72–74 (1994) Demetrick et al.; Chromosome Res. 3 (4), 261–262 (1995) Mitchel et al.; Nature Genet. 12 (1), 97–99 (1996) Zuo, L.; rice cdc2 in GenBank Accession No. X60375 and Mol. Gen. Genet. 233 (1–2), 10–16 (1992), Hashimoto et al.; maize cdc2 in GenBank Accession No. M60526 and Proc. Natl. Acad. Sci. U.S.A. 88, 3377–3381 (1991) Colassanti et al.; *Homo sapiens* cdk7 in GenBank Accession No. NM 001799 and Oncogene 9(11), 3127–3138 (1998) Darbon et al.; tobacco CycD in GenBank Accession No. AJ011894, AJ011893, AJ011892, and Plant Physiol. 119, 343–351 (1999) Murray, J. A. H.; pea CycD in GenBank Accession No. AB008188 and Plant Cell Physiol. 39 (3), 255–262 (1998) Shimizu, S. and Mori, H.; *Arabidopsis* CycD in GenBank Accession No. X83369, X83370 and X83371 and Plant Cell 7 (1), 85–103 (1995) Murray, J. A. H.; *C. rubrum* CycD in GenBank Accession No. Y10162 Renz et al.; human CycE in GenBank Accession No. L48996 and Proc. Natl. Acad. Sci. U.S.A. 92 (26), 12146–12150 (1995) Ohtani et al.; *D. melanogaster* CycE type 1 in GenBank Accession No. X75026 and X75027 and Development 119 (3), 673–690 (1993) Richardson H. E. et al; wheat E2F in GenBank Accession No. AJ238590 and Nucleic Acids Res. 27, 3427–3533 (1999) Ramirez-Parra, E.; tobacco E2F in GenBank Accession No. AB025347 and FEBS Lett. 460, 117–122 (1999) Sekine, M.; Rb in GenBank Accession No. A68394 and WO 9747647 Gutierrez A. C.; RRB2b and RRB2ba in GenBank Accession No. AF007795 and Mol. Cell. Biol. 17 (9), 5077–5086 (1997) Ach, R. A. et al; *Zea mays* Rb1 in GenBank Accession No. X98923 and Embo J. 15 (18), 4900–4908 (1996) Xie, Q. et al; ZmRb in GenBank Accession No. U52099 Grafi, G. et al; Arabidopsis CKI in WO 99/14331, U.S. Ser. No. 60/119,857 filed Feb. 12, 1999; U.S. Ser. No. 09/398,858 filed Sep. 20, 1999, U.S. Ser. No. 60/119,857 filed Feb. 12, 1999; and U.S. Ser. No. 09/257,131 filed Feb. 25, 1999 the disclosures of which are incorporated herein by reference.

Because CycE can stimulate progression of cells into S phase, increasing CycE activity may be useful in terms of increasing integration frequencies during the transformation process. Stimulation of the G1/S transition results in increased cell division in certain cases, and in this regard, use of CycE to stimulate cell division may stimulate callus growth and/or growth in the whole plant (or in specific tissues where this activity is targeted).

We have successfully used the maize Cyclin D (CycD) gene for transformation improvement. In GS3, transformation frequency was found to improve by 2 to 3-fold when a ZmCycD gene was used. In order to obtain even higher transformation frequency and/or genotype independent transformation improvement, identification and manipulation of such factors is useful.

The Rb/E2F pathway is a key control mechanism for G1/S progression in most eukaryotic cells. Cyclin D is a key positive regulator of the G1/S transition, bringing CDK4/6 to the vicinity of Rb/E2F and initiating the phosphorylation of Rb. Cyclin E continues this process by recruiting CDK2 to form an active complex, which completes the phosphorylation of Rb. Phosphorylation of Rb protein is necessary to release E2F for G1/S transition. Recent evidence suggests that CycD/CDK4 or 6 mainly inhibit Rb-HDAC interaction (interactions between Rb and histone deacetylases) whereas CycE/CDK2 directly inhibits Rb-E2F interaction.

Rb represses S-phase entry through two mechanisms: i) binding to and inactivating E2F, and ii) recruiting HDAC to participate in chromatin remodeling. Both E2F and HDAC bind to the A-B pocket of Rb. Disruption of the A-B pocket leads to an inactive Rb. The C-domain in Rb provides docking sites for CycD and CycE. Initial phosphorylation of the C-domain by CyD/CDK4 or 6 leads to an intramolecular binding of the C-domain to the pocket, specifically, to the lysine patch surrounding the LXCXE binding site in domain B. This intramolecular interaction inhibits the binding of HDAC to the pocket and promotes the access of CycE/CDK2 to phospho-acceptor sites in the B-domain. Progressive phosphorylation of these B-domain phosphorylation sites by CycE/CDK2 completes the hyperphosphorylation of Rb. More importantly, phosphorylation of S-567 by CycE/CDK2 leads to disruption of the A-B pocket, inhibition of the interaction between Rb and E2F, and thus to a stimulation of the G1/S transition.

Therefore, the CycE nucleic acid is a key positive regulator for S-phase entry. Manipulation of plant CycE nucleic acids will improve transformation, especially when used together with the Cyclin D gene. CycE expression stimulates the G1-S phase transition, and will thus increase integration frequencies upon introduction of DNA into these cells. Expression of CycE will also provide a positive growth advantage in transgenic cells (relative to non-transformed tissues), thus providing a method for positive selection of transformants based on differential growth rates.

CycE appears to be an important component in the endoreduplication process in Drosophila. Appropriately enhanced CycE overexpression may stimulate the endoreduplication process in maize, and could be used to purposefully stimulate endoreduplication in tissues where this process normally does not occur, or to enhance this process in cells and/or tissues that normally undergo endoreduplication.

CycE may increase crop yield, growth and biomass accumulation. CycE expression could stimulate cell division in specific tissues (under control of a promoter specific to said tissue), increasing the relative growth of the targeted tissue (i.e. increased vegetative growth in the stem and/or leaves, increased ear size, kernel size, etc). The sequence could also be used to block division in certain cells (i.e. as a sterility method) using the CycE sequence in such well-known methods as antisense expression, co-suppression or hairpin technology to silence endogenous CycE expression.

Other more specialized applications exist for these genes at the whole plant level. It has been demonstrated that endoreduplication occurs in numerous cell types within plants, but this is particularly prevalent in maize endosperm, the primary seed storage tissue. Under the direction of endosperm-specific promoters, expression of CycE genes (and possibly expression of CycE in conjunction with genes that inhibit mitosis) will further stimulate the process of endoreduplication.

In addition to the positive influence of transient cell cycle stimulation, stable expression of positive cell cycle regulators would be a benefit for positive selection schemes in the recovery of transgenic plants and plant cells. In a population of cells and/or callus growing in vitro, cells expressing a gene such as CycE will have a differential growth advantage based simply on their accelerated division rate. It would be expected that these transgenic cells or cell/clusters would grow more rapidly than their non-transformed counterparts in culture, permitting ready identification of transformants.

Such a positive growth advantage (imparted by expression of a gene such as CycE, or CycE plus another cell cycle component), would also be beneficial in other types of transformation strategies, including as examples, protoplast transformation, leaf base transformation and transformation of cells in meristems. Such growth stimulation may also extend transformation protocols to tissues normally no amenable to culture. Examples would include such tissues as portions of leaves (in which the cells do not normally divide), scutellum from recalcitrant inbreds (in which cells typically are not induced to divide in culture), cambial tissues, and nodal tissues, etc.

Of particular interest is the use of cell cycle genes such as CycE to impart a positive growth advantage to cells in the meristem, including apical initials. The apical initials in angiosperm shoot meristems are defined by their position within the meristem. If an apical initial cell becomes compromised relative to neighboring cells in the meristem, it will be replaced by an adjacent neighbor that is not at a disadvantage. This new cell assumes the role of the apical initial. Conversely, transgenic cells adjacent to the apical initials with a positive growth advantage can, over time (i.e. through successive cell generations), out-compete the wild-type apical initials, eventually replacing these cells and establishing a homogeneous transformed meristem. There can also be organ and/or whole plant impacts to such cell cycle transgene expression.

References

Harbour J W, R B Luo, A D Santi, A A Postigo, and D C Dean 1999, Cdk phosphorylation triggers sequential intramolecular interactions that progressively block Rb functions as cells move through G1. Cell 98:859–869.

Geng Y, W Whoriskey, M Y Park, R T Bronson, R H Medema, T Li, R A Weinberg, and P Sicinski 1999, Rescue of Cyclin D1 deficiency by knocking Cyclin E. Cell 97:767–777.

Brehm A, E A Miska, D J McCance, J L Reid, A J Bannister, and T Kouzarides 1998, Retinoblastoma protein recruits histone deacetylase to repress transcription. Nature 391:597–601.

Magnaghi-Jaulin L, R Groisman, I Naguibneva, P Robin, S Lorain, J P Le Villain, F Troalen, D Trouche, and A Harel-Bellan 1998, Retinoblastoma protein represses transcription by recruiting a histone deacetylase. Nature 391:601–605.

Lundberg A S and R A Weinberg 1998, Functional inactivation of the retinoblastoma protein requires sequential modification by at least two distinct cyclin-cdk complexes. MCB 18:753–761.

Adam P D, X Li, W R Sellers, K B Baker, X Leng, J W Harper, Y Taya, and W G Kevin, JR. 1999, Retinoblastoma protein contains a C-terminal motif that targets it for phosphorylation by Cyclin-cdk complexes. MCB 19:1068–1080.

Lee J-O, A A Russo, and N P Pavletich 1998, Structure of the retinoblastoma tumor-suppressor pocket domain bound to a peptide from HPV E7. Nature 391:859–865.

Gudas J M, M Payton, S Thukral, E Chen, M Bass, M O Robinson, and S Coats 1999, Cyclin E2, a novel G1 cyclin that binds Cdk2 and is aberrantly expressed in human cancers. MCB 19:612–622.

Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In preferred embodiments the monocot is corn, sorghum, barley, wheat, millet, or rice. Preferred dicots include soybeans, sunflower, safflower, canola, alfalfa, cotton, potato, or cassava.

Functional fragments included in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), DIRECTED MUTAGENESIS: A Practical approach, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences. Such changes will alter, add or delete a single amino acid or a small percentage of amino acids in the encoded sequence. Variants are referred to as "conservatively modified variants" where the alteration results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J.-H., et al. Proc. Natl. Acad. Sci. USA 94:4504–4509 (1997).

The present invention also includes the use of 5' and/or 3' UTR regions for modulation of translation of heterologous coding sequences. Positive sequence motifs include translational initiation consensus sequences (Kozak, Nucleic Acids Res. 15: 8125 (1987)) and the 7-methylguanosine cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., Mol. and Cell. Biol. 8:284 (1988)).

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., Nucleic Acids Res. 12:387–395 (1984)) or MacVector 4.1 (Eastman Kodak Co., New Haven, Conn.).

For example, the inventive nucleic acids can be optimized for enhanced expression in organisms of interest. See, for example, EPA0359472; WO91/16432; Perlak et al. (1991) Proc. Natl. Acad. Sci. USA 88:3324–3328; and Murray et al. (1989) Nucleic Acids Res. 17:477–498. In this manner, the genes can be synthesized utilizing species-preferred codons. See, for example, Murray et al. (1989) Nucleic Acids Res. 17:477–498, the disclosure of which is incorporated herein by reference.

The present invention provides subsequences comprising isolated nucleic acids containing at least 20 contiguous bases of the inventive sequences. For example the isolated nucleic acid includes those comprising at least 25, 30, 35, 40, 45, 50, 55, 60, 70, 80, 90, or 100 or more contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-lnterscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'–3' (Paoli, Pa.). See also, U.S. Pat. Nos. 5,614,391;and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-lnterscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics*, 37:327–336 (1996). Other methods for producing full-length libraries are known in the art. See, e.g., Edery et al., *Mol. Cell Biol.*, 15(6):3363–3371 (1995); and, PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685 and 5,637,685; and Soares et al., *Proc. Natl. Acad. Sci. USA*, 91:9228–9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-lnterscience, New York (1995); and, Swaroop et al., *Nucl. Acids Res.*, 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-lnterscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

For purposes of defining the invention, the hybridization is preferably conducted under low stringency conditions which include hybridization with a buffer solution of 30% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. More preferably the hybridization is conducted under moderate stringency conditions which include hybridization in 40% formamide, 1 M NaCl, 1% SDS at 37° C., and a wash in 0.5× to 1×SSC at 55° C. Most preferably the hybridization is conducted under high stringency conditions which include hybridization in 50% formamide, 1 M NaCl, 1% SDS at 37° C., and a wash in 0.1×SSC at 60° C. The time for conducting the hybridization is not critical and is generally in the range of from 4 to 16 hours.

An extensive guide to the hybridization of nucleic acids is found in Tijssen, *Laboratory Techniques in Biochemistry and Molecular Biology—Hybridization with Nucleic Acid Probes*, Part I, Chapter 2 "*Overview of principles of hybridization and the strategy of nucleic acid probe assays*", Elsevier, N.Y. (1993); and *Current Protocols in Molecular Biology*, Chapter 2, Ausubel, et al., Eds., Greene Publishing and Wiley-lnterscience, New York (1995). Often, cDNA libraries will be normalized to increase the representation of relatively rare cDNAs.

The nucleic acids of the invention can be amplified from plant nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

The nucleic acid library can be a cDNA library, a genomic library, or a library generally constructed from nuclear transcripts at any stage of intron processing. Libraries can be made from a variety of plant tissues. Good results have been obtained using mitotically active tissues such as shoot meristems, shoot meristem cultures, embryos, callus and suspension cultures, immature ears and tassels, and young seedlings. The cDNA of the present invention was obtained from developing maize endosperm. Since cell cycle proteins are typically expressed at specific cell cycle stages it may be possible to enrich for such rare messages using exemplary cell cycle inhibitors such as aphidicolin, hydroxyurea, mimosine, and double-phosphate starvation methods to block cells at the G1/S boundary. Cells can also be blocked at this stage using the double phosphate starvation method. Hormone treatments that stimulate cell division, for example cytokinin, would also increase expression of the cell cycle RNA.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997).

The sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.), and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Expression Cassettes

The present invention also includes expression cassettes comprising isolated nucleic acids of the present invention. An expression cassette will typically comprise a polynucleotide of the present invention operably linked to transcriptional initiation regulatory sequences which will direct the transcription of the polynucleotide in the intended host cell, such as tissues of a transformed plant. Plant expression vectors may also include selectable marker.

The construction of expression cassettes that can be employed in conjunction with the present invention is well known to those of skill in the art in light of the present disclosure. See, e.g., Sambrook et al.; *Molecular Cloning: A Laboratory Manual*; Cold Spring Harbor, N.Y.; (1989); Gelvin et al.; *Plant Molecular Biology Manual*; (1990); *Plant Biotechnology: Commercial Prospects and Problems*, eds. Prakash et al.; Oxford & IBH Publishing Co.; New Delhi, India; (1993); and Heslot et al; *Molecular Biology and Genetic Engineering of Yeasts*; CRC Press, Inc., USA; (1992); each incorporated herein in its entirety by reference.

Suitable promoter regulatory regions generally include a transcription initiation start site, a ribosome-binding site, an RNA processing signal, a transcription termination site, and/or a polyadenylation signal. Useful promoters can confer inducible, constitutive, environmentally- or developmentally-regulated, or cell- or tissue-preferred/selective expression.

Examples of constitutive promoters include the cauliflower mosaic virus (CaMV) 35S transcription initiation region, the 1'- or 2'- promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter that is inducible by hypoxia or cold stress, the Hsp70 promoter which is inducible by heat stress, and the PPDK promoter which is inducible by light. Also useful are promoters that are chemically inducible. Inducing expression immediately after DNA introduction will improve integration and promote a growth response caused by the induced gene. Inducing the gene at a later time will cause a differential growth response.

Examples of promoters under developmental control include promoters that initiate transcription preferentially in certain tissues, such as leaves, roots, fruit, seeds, or flowers. An anther specific promoter 5126 is disclosed in (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47, 95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18(21), 6426 (1990). See the following site relating to the waxy promoter: Kloesgen, R. B., Gierl, A., Schwarz-Sommer, Z S. and Saedler, H., Molecular analysis of the waxy locus of Zea mays, *Mol. Gen. Genet.* 203, 237–244 (1986). Promoters that express in the embryo, pericarp, and endosperm are disclosed in U.S. applications Ser. Nos. 60/097,233 filed Aug. 20, 1998 and 60/098,230 filed Aug. 28, 1998. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of the polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395–4405 (1988); Callis et al., *Genes Dev.* 1:1183–1200 (1987). Use of maize introns Adh1-S intron 1,2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene, which confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol., 153:253–277 (1987). Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Nat'l. Acad. Sci.* (*USA*) 85:8805–8809 (1988); and Hiatt et al., U.S. Pat. No. 4,801,340.

Another method of suppression is sense suppression, or cosuppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990) and U.S. Pat. No. 5,034,323.

Gene expression can also be down-regulated by means of hairpin technology, Waterhouse et al. Proc. Natl. Acad. Sci. USA 95 pp. 1359–1364 (1998); Selker, Cell, Vol. 97, 157–160, Apr. 16, 1999; Grant, Cell, Vol. 96, 303–306, Feb. 5, 1999. Another method of down-regulation of the protein involves using PEST sequences that provide a target for degradation of the protein.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585–591 (1988).

A variety of cross-linking agents, alkylating agents and radical generating species as pendant groups on polynucleotides of the present invention can be used to bind, label, detect, and/or cleave nucleic acids. For example, Vlassov et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer et al., *J Am Chem Soc* (1989) 111:8517–8519, effect covalent crosslinking to a target nucleotide using an alkylating agent complementary to the single-stranded target nucleotide sequence. A photo-activated crosslinking to single-stranded oligonucleotides mediated by psoralen was disclosed by Lee et al., *Biochemistry* (1988) 27:3197–3203. Use of crosslinking in triple-helix forming probes was also disclosed by Home et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

Proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

If the enzyme activity is to be maintained, mutations made in the DNA encoding the variant protein should not place the sequence out of reading frame and preferably will not create complementary regions that could produce secondary mRNA structure. See EP Patent Application Publication No. 75,444.

The isolated proteins of the present invention include a polypeptide comprising at least 23 contiguous amino acids encoded by any one of the nucleic acids of the present invention, or polypeptides that are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, 40, 45 amino acids in length, often at least 50, 60, 70, 80, or 90 amino acids in length.

The present invention includes catalytically active polypeptides (i.e., enzymes). Catalytically active polypeptides will generally have a specific activity of at least 20%, 30%, or 40%, and preferably at least 50%, 60%, or 70%, and most preferably at least 80%, 90%, or 95% that of the native (non-synthetic), endogenous polypeptide. The invention also includes polypeptides with much higher activity than the native protein.

Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

The present invention includes modifications that can be made to an inventive protein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A protein of the present invention can be expressed in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the nucleic acid of interest can be isolated in significant quantities for introduction into the desired plant cells.

Host cells that can be used in the practice of this invention include prokaryotes, including bacterial hosts such as *Eschericia coli*, *Salmonella typhimurium*, and *Serratia marcescens*. Eukaryotic hosts such as yeast or filamentous fungi may also be used in this invention. It preferred to use plant promoters that do not cause expression of the polypeptide in bacteria.

Commonly used prokaryotic control sequences include promoters such as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and *Salmonella* (Palva, et al., Gene 22:229–235 (1983); Mosbach, et al., Nature 302: 543–545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology*. Vol. 2: *Special Methods in Peptide Synthesis, Part A.;* Merrifield et al., *J. Am. Chem. Soc.* 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

The proteins of this invention may be purified to substantial purity by standard techniques well known in the art, including detergent solubilization, selective precipitation with such substances as ammonium sulfate, column chromatography, immunopurification methods, and others.

See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation of the polypeptides can be effected by increasing or decreasing the concentration and/or the composition of the polypeptides in a plant. The method comprises transforming a plant cell with an expression cassette comprising a polynucleotide of the present invention to obtain a transformed plant cell, growing the transformed plant cell under plant forming conditions, and inducing expression of the polynucleotide in the plant for a time sufficient to modulate concentration and/or composition of the polypeptides in the plant or plant part.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868.

In particular, modulating cell cycle proteins are expected to provide a positive growth advantage and increase crop yield. Cell cycle nucleic acids can be adducted to a second nucleic acid sequence encoding a DNA-binding domain, for use in two-hybrid systems to identify interacting proteins. It is expected that modulating the level of cell cycle protein, i.e. overexpression in conjunction with overexpression of G1/S transition-stimulating genes, will increase endoreduplication. Endoreduplication is expected to increase the size of the seed, the size of the endosperm and the amount of protein in the seed.

An isolated nucleic acid (e.g., a vector) comprising a promoter sequence can be transfected into a plant cell. Subsequently, a plant cell comprising the isolated nucleic acid is selected for by means known to those of skill in the art such as, but not limited to, Southern blot, DNA sequencing, or PCR analysis using primers specific to the promoter and to the nucleic acid and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration of the polypeptides is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development.

Modulating nucleic acid expression temporally and/or in particular tissues can be controlled by employing the appropriate promoter operably linked to a polynucleotide of the present invention in, for example, sense or antisense orientation as discussed in greater detail above. Induction of expression of a polynucleotide of the present invention can also be controlled by exogenous administration of an effective amount of inducing compound. Inducible promoters and inducing compounds that activate expression from these promoters are well known in the art.

In preferred embodiments, the polypeptides of the present invention are modulated in monocots or dicots, preferably corn, soybean, sunflower, safflower, sorghum, canola, wheat, alfalfa, cotton, rice, barley and millet.

Means of detecting the proteins of the present invention are not critical aspects of the present invention. In a preferred embodiment, the proteins are detected and/or quantified using any of a number of well-recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B. V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods for detecting proteins include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule that is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Methods of measuring enzyme kinetics are well known in the art. See, e.g., Segel, *Biochemical Calculations*, 2nd ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, Nature 256:495–497 (1975).

Other suitable techniques involve selection of libraries of recombinant antibodies in phage or similar vectors (see, e.g., Huse et al., Science 246:1275–1281 (1989); and Ward, et al., Nature 341:544–546 (1989); and Vaughan et al., Nature Biotechnology, 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., Nature Biotech., 14:845–851 (1996). Also, recombinant immunoglobulins may be produced. See, Cabilly, U.S. Pat. No. 4,816,567; and Queen et al., Proc. Nat'l Acad. Sci. 86:10029–10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance, which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transfection/Transformation of Cells

The method of transformation/transfection is not critical to the present invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide of the present invention can be used to construct an expression cassette that can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet.* 22:421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp. 197–213 in Plant Cell, Tissue and Organ Culture, Fundamental Methods. eds. O. L. Gamborg and G. C. Phillips. Springer-Verlag Berlin Heidelberg N.Y., 1995. The introduction of DNA constructs using polyethylene glycol precipitation is described in Paszkowski et al., *Embo J.* 3:2717–2722 (1984). Electroporation techniques are described in Fromm et al., *Proc. Natl. Acad. Sci.* 82:5824 (1985). Ballistic transformation techniques are described in Klein et al., Nature 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,981,840. *Agrobacterium tumefaciens*-meditated transformation techniques are well described in the scientific literature. See, for example Horsch et al., Science 233:496–498 (1984), and Fraley et al., *Proc. Natl. Acad. Sci.* 80:4803 (1983). For instance, *Agrobacterium* transformation of maize is described in WO 98/32326. *Agrobacterium* transformation of soybean is described in U.S. Pat. No. 5,563,055.

Other methods of transfection or transformation include (1) *Agrobacterium rhizogenes*-mediated transformation (see, e.g., Lichtenstein and Fuller In: Genetic Engineering, Vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25:1353, (1984)), (3) the vortexing method (see, e.g., Kindle, *Proc. Natl. Acad. Sci. USA* 87:1228, (1990)).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding polynucleotides can be obtained by injection of the DNA into reproductive organs of a plant as described by Pena et al., Nature, 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Stable transformation of some gene products into recipient cells is problematic for regulatory and other reasons. Therefore, it is desirable to transiently express proteins in transformed cells. Using *Agrobacterium* as a protein vector for transient expression is potentially simpler and would deliver a selected protein and a desired transgene to the same cell simultaneously.

Certain species of symbiotic micro-organisms are known to transfer T-DNA into recipient cells by a mechanism similar to bacterial conjugation. T-DNA traverses the bacterial membranes, the cell wall and cell membranes, and the nuclear membrane before integrating into the host genome through illegitimate recombination. Numerous bacterial proteins are also included in these processes and have been characterized. Among these proteins are at least three gene products from *Agrobacterium*: VirD2, VirE2, and VirF which are transcribed from the virulence region of the Ti plasmid and transferred directly into plant cells.

VirD2 encodes a multifunctional protein which participates in the endonucleolytic cleavage of the T-DNA border sequences, the ligation of the left border nick for replacement strand synthesis, nuclear import of the T-complex, and precise integration of the 5' end of T-DNA into the host genome. VirD2 establishes a covalent association with the T-DNA between a specific right-border (RB) nucleotide and Tyr-29 of the protein.

VirE2 encodes a multifunctional protein that has single-stranded DNA binding (SSB) activity and coats the T-strand. VirE2 is also likely to be involved both in nuclear import and with the integration of full-length T-DNA into the host genome. VirE2 is the most abundant of Vir proteins with 350 to 700 copies thought to be required to coat a 20 kb T-strand.

The function of the VirF gene product is unknown. The coding sequence is present in octopine strains but not in nopaline strains. Complementation of nopaline strains or VirF mutants of octopine strains extends host range.

VirE2 is the most preferred product for use as a delivery protein fusion vector. First, it is produced in high abundance. Second, it can be transmitted separately from the T-strand to plant cells. VirD2, in contrast, is covalently associated with the T-strand. Third, VirE2 has been studied intensively and functional domains are known. Relatively little information is available for VirF.

Proteins delivered from *Agrobacterium* plasmids into plant cells are in the form of fusions with the *Agrobacterium* virulence proteins. Fusions are constructed between a selected gene and genes for bacterial virulence proteins such as VirE2, VirD2, or VirF which are located outside the T-DNA borders. This leaves an expression cassette within the borders available for genes that are to be stably transformed. Fusions are constructed to retain both those properties of bacterial virulence proteins required to mediate delivery into plant cells and the selected activity required for altering cell function. This method ensures a high frequency of simultaneous co-delivery of T-DNA and the functional selected protein into the same host cell.

An example is the delivery of a VirE2::"cell cycle protein" fusion to plant cells. Several candidate genes that might stimulate the G1→S transition are available. Examples are well known in the art such as cyclins (P. W. Doerner, Cell Cycle Regulation in Plants, Plant Physiol. (1994) 106:823–827.), and the gemini virus RepA gene (U.S. Ser. No. 09/257,131). The promotion of S phase by transient "expression" of selected cell cycle proteins may enhance integration of the coresident T-DNA. Other fusion partners and applications of protein delivery are conceivable.

The method can be used to test the efficacy of visible selectable markers such as GFP (Haseloff et al, *Trends in Genetics* 11(8):328–329 (1995), GUS (beta-gluconronidase), and Luciferase, (Visser et al., *Biochemistry* 24(6):1489–1496 (1985). Or the visible markers could be used in the system to test changes in protocols that would enhance transfer of molecules to various plant cells, or cells or tissues of recalcitrant species.

Using the method with selected proteins such as Bcl-2 (Pegoraro et al., *Proc. Nat. Ac. Sci* 81(22):7166–7170 (1984), or IAP (inhibitor of apoptosis) (Crook, et al., *Journ. Vir*. 67(4):2168–2174 (1993), would reduce the tendency of recently transformed cells to undergo programmed cell death, and in the process increase transgene integration and overall transformation frequencies.

Fusing the delivery protein to genes such as fus3 (Elion et al., *Cell* 60(4):649–664 (1990), CLAVATA (Clark et al., *Development (Cambridge)* 122(5):1567–1575 (1996), KNOTTED-1 (Lowe et al., *Genetics* 132(3):813–822 (1992), or pk1 (Ogas et al, *Science* (Washington D.C.) 277(5322):91–94 (1997) would commit cells and cell lineages to a desired developmental fate such as meristem development or stimulating embryo development.

Introduction of a site-specific recombinase protein system such as FLP/RFT (U.S. Ser. No. 08/972,258) or Cre/loxP (Abremski-K. et al., *Jour. Mol. Bio*. 184(2):211–220, 1985) into plant cells could be used to catalyze a variety of recombination-mediated alterations. For example, sequence excision could be used to remove one transgene while activating a second. Recombinase-mediated integration, gene replacement and genomic exchanges could also be mediated through introduction of such functional fusion proteins.

The method can also be practiced with other strains of bacteria known to deliver protein into cells. Examples are: Rhizobium sp., Phyllobacterium sp., or any other bacterium of the Rhizobiaceae taxa that transfer proteins to recipient cells.

The method could be extended to employ multiple delivery protein fusions on the same, or coresident, binaries. This would conceivably allow the transient activity of "protein cocktails" mediating complex functions or pathways related to transformation objectives.

The *Argrobacterium* strategy is potentially simpler than methods to achieve transient-only expression using current direct delivery methods such as microinjection, bombardment, electroporation or silica fiber methods.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by *Argrobacterium* can be achieved as described by Horsch et al., *Science*, 227:1229–1231 (1985) and Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant are also contemplated.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants that can be used in the method of the invention include monocotyledonous and dicotyledonous plants. Preferred plants include corn, soybean, sunflower, safflower, sorghum, canola, wheat, alfalfa, cotton, rice, barley and millet. Seeds derived from plants regenerated from transformed plant cells, plant parts or plant tissues, or progeny derived from the regenerated transformed plants, may be used directly as feed or food, or further processing may occur.

The present nucleic acids and proteins have many uses. They can be used to identify other interacting proteins involved in cell cycle regulation. They can be used to provide antigenic proteins. Altering the expression of the present nucleic acids and proteins provides a method for modulating cell division, especially for increasing the number of cells undergoing cell division. This has been found useful in improving transformation efficiency.

Use in Two-Hybrid Systems

An important utility for the maize CycE genes that have been cloned in the genetic approach of using a two-hybrid system to identify interacting proteins (i.e. proteins that specifically interact with the CycE gene-encoded products. This method, typically done using the yeast *Saccharomyces cerevisiae*, exploits the fact that a functional transcription factor can be separated into two components; a DNA-binding factor and an activation domain, which when held together non-covalently will still bind DNA and activate transcription.

The test system is constructed as follows: a DNA-binding domain is localized 5' to a reporter gene, for example luciferase, and this cassette is transformed into a yeast strain. The nucleic acid sequence for the DNA-binding domain of the transcriptional factor is ligated to the gene (or partial gene sequence) being used as bait. Expression of this DNA-binding domain-bait fusion is driven, for example by the yeast adh1 promoter. A "library" of gene-fusions is also produced, using the activation domain of the transcriptional factor fused to genes (or gene fragments) from an expression library of interest (referred to as the activation domain hybrid). Expression of the activation domain hybrids is also accomplished, for example, using the yeast adh1 promoter.

To perform the two-hybrid screen, plasmids encoding the DNA-binding domain hybrid and a library of activation domain hybrids are introduced (sequentially or simultaneously) into a yeast strain already containing the inactive reporter. Transformed yeast in which the activation domain hybrid specifically binds to the DNA-binding domain hybrid will express luciferase. Positives are further characterized by sequence analysis, and further tests of relevance of biological interactions.

Commonly used DNA-binding domains include those from lexa protein in *E. coli*, and the Ga14 protein in yeast. Likewise, commonly used activation domains include B42 (bacterial) and Ga14 (yeast). For details, see Hannon G, and Bartel P, *Identification of interacting proteins using the two-hybrid system, Methods Mol. Cellular Biol.* 5:289–297 (1995).

The nucleic acids and proteins of the present invention modulate the rate of cell division and the total number of cells. Increasing the total number of cells in a plant is expected to increase crop yield. It is also expected that the present invention provides a method for modulating plant height or size. The present invention provides a method for modulating cell growth. In particular it is expected that the present inventive nucleic acids and proteins will provide a method for increasing the growth rate and providing a positive growth advantage in a plant. The present invention is expected to provide a method for enhancing or inhibiting organ growth, for example seed, root, shoot, ear, tassel, stalk, pollen, stamen. Therefore, the nucleic acids and proteins of the present invention may provide a method for producing organ ablation, such as for parthenocarpic fruits or male sterile plants. The nucleic acids and proteins can be used to increase the number of pods per plant and/or seeds/pod or ear. The nucleic acids and proteins of the present invention may provide a method for altering the lag time in seed development. The nucleic acids of the present invention are expected to provide a method for improving in cells the response to environmental stress such as drought, heat, or cold.

The nucleic acids and proteins of the present invention provide a method for enhancing embryogenic response, i.e. size or growth rate. They are also expected to provide a method for increasing callus induction. The nucleic acids and proteins of the present invention should provide a method for positive selection and/or increasing plant regeneration. The nucleic acids and proteins of the present invention may provide a method for altering the percent of cells that are arrested or for altering the amount of time a cell spends in a particular cell cycle, i.e. in G1 or G0 stages of the cell cycle. The nucleic acids and proteins of the present invention should provide hormone independent cell growth. The nucleic acids and proteins of the present invention may also provide a method for increasing growth rate of cells in bioreactors.

All cited publications are incorporated herein by reference.

Although the present invention has been described in some detail by way of illustration and example for purposes of clarity of understanding, it will be obvious that certain changes and modifications may be practiced within the scope of the appended claims.

EXAMPLES

Example 1

Isolation of Maize CycE Genes

Total RNA was isolated from corn tissues with TRIzol Reagent (Life Technology Inc. Gaithersburg, Md.) using a modification of the guanidine isothiocyanate/acid-phenol procedure described by Chomczynski and Sacchi [Chomczynski, P., and Sacchi, N., *Anal. Biochem.* 162, 156 (1987)]. In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATract system (Promega Corporation. Madison, Wis.). In brief, biotinylated oligo(dT) primers were used to hybridize to the 3' poly(A') tails on mRNA. The hybrids were captured using streptavidin coupled to paramagnetic particles and a magnetic separation stand. The mRNA was washed using high stringency conditions and eluted using RNAase-free deionized water.

cDNA Library Construction:

cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between Not I and Sal I sites. Mitotically active tissues from *Zea mays* were employed, including such sources as shoot cultures, immature inflorescences (tassel and ear) as well as other sources of vegetative meristems.

Sequencing Template Preparation:

Individual colonies were picked and DNA was prepared either by PCR with M13 forward primers and M13 reverse primers, or by plasmid isolation. All the cDNA clones were initially sequenced using M13 reverse primers. As additional fragments of the genes were discovered, new sequencing primers were designed.

*PROTOCOLS*, Murray (ed.), pages 271–281 (Humana Press, Inc. 1991). Functional fragments of the cell cycle protein are identified by their ability, upon introduction to cells, to stimulate the G1 to S-phase transition, which is manifested by increased DNA replication in a population of cells and by increased cell division rates.

5'-RACE

Library RACE was performed using several of Pioneer's maize libraries. 5' RACE was done using a cDNA library constructed from leaves and stems of maize plants at the three-leaf stage. The principal of 5' RACE is described in detail in numerous publications such as: Frohman M. A., 1993, Rapid Amplification of Complementary DNA Ends for Generation of Full-Length Complementary DNAs: Thermal RACE. In: Methods in Enzymology, vol. 28, pp 340–356. Detailed procedure can be found in the ClonTech Marathon cloning manual.

Example 2

Using CycE's in a Two-hybrid System to Identify Maize Cell Cycle Genes

CycE gene expression during the G1→S transition and early S-phase plays a prominent role in progression through the cell cycle. The proteins encoded by the CycE gene family are an important part of the complex that binds and phosphorylates retinoblastoma-associated gene family members. In turn, Rb releases E2F and this transcription factor starts the cascade of events leading to DNA replication. As such, the CycE genes and their encoded proteins can be used to identify other cell cycle regulatory proteins. This can be done using the CycE gene as bait (the target fused to the DNA-binding domain) in a yeast two-hybrid screen. Methods for two-hybrid library construction, cloning of the reporter gene, cloning of the DNA-binding and activation domain hybrid gene cassettes, yeast culture, and transformation of the yeast are all done according to well-established methods (see Sambrook et al., 1990; Ausubel et al., 1990; Hannon and Bartels, 1995). Using this method, *Zea mays* Cdk2 and Rb genes are identified as components of the activation domain hybrid, and are confirmed through further sequence analysis. Similarly, inhibitors of the Cdk2/CycE complex such as the CIP/KIP family (p21, p27, p57), and enhancers of the Cdk2/CycE complex similar to p37 are identified.

Example 3

CycE-bound Affinity Columns for Identifying Cdk2 Proteins and their Encoding Genes Purified recombinant CycE protein can be immobilized on a matrix via a covalent crosslinking or affinity purification as described supra. This matrix can then be used to pull-down proteins that interact with CycE proteins, inter alia, cyclin-dependent kinase. CDK activity can then be assessed by measuring the addition of radioactive phosphorus to protein-substrates and CDK protein levels determined by immunoassay. Additionally, this can be used to purify the CDK activity present in different plant tissues and protein fractions. The presence and level of other CycE interacting proteins can also be determined on the basis of immunological assay, activity quantification, SDS-PAGE analysis and other methods. These measures can then be correlated with the reproductive state, capacity for division, developmental stage, or the quality of different samples. A CycE nucleic acid can also be adducted to a second nucleic acid sequence encoding a DNA-binding domain in order to identify CycE interacting proteins.

Example 4

Using the CycE Gene to Improve Maize Transformation

Delivery of the ZmCycE gene can be accomplished through numerous well-established methods for plant cells, including for example particle bombardment, sonication, PEG treatment or electroporation of protoplasts, electroporation of intact tissue, silica-fiber methods, microinjection or *Agrobacterium*-mediated transformation. Using one of the above methods, DNA is introduced into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids. For target tissues receiving the CycE expression cassette, transformation frequency is improved.

Particle-mediated DNA Delivery

The CycE gene (ZmCycE) is cloned into a cassette with a constitutive promoter (the maize ubiquitin promoter, UBI, including the first ubiquitin intron) and a 3' sequence from the potato proteinase inhibitor (pinII). Particle bombardment is used to introduce the UBI::ZmCycE::pinII-containing plasmid along with a UBI::PAT~GFP::pinII-containing plasmid (which, when expressed produces a functional PAT~GFP fusion protein which confers bialaphos resistance and green fluorescence) into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids. Ears are harvested at approximately 10 days post-pollination, and 1.2–1.5 mm immature embryos are isolated from the kernels, and placed scutellum-side down on maize culture medium.

The immature embryos are bombarded from 18–72 hours after being harvested from the ear. Between 6 and 18 hours prior to bombardment, the immature embryos are placed on medium with additional osmoticum (MS basal medium, Musashige and Skoog, 1962, *Physiol. Plant* 15:473–497, with 0.25 M sorbitol). The embryos on the high-osmotic medium are used as the bombardment target, and are left on this medium for an additional 18 hours after bombardment.

For particle bombardment, plasmid DNA (described above) is precipitated onto 1.8 μm tungsten particles using standard $CaCl_2$-spermidine chemistry (see, for example, Klein et al., 1987, *Nature* 327:70–73). Each plate is bombarded once at 600 PSI, using a DuPont Helium Gun (Lowe et al., 1995, *Bio/Technol* 13:677–682). For typical media formulations used for maize immature embryo isolation, callus initiation, callus proliferation and regeneration of plants, see Armstrong, C., 1994, In "The Maize Handbook", M. Freeling and V. Walbot, eds. Springer Verlag, NY, pp 663–671.

Selection

Within 1–7 days after particle bombardment, the embryos are moved onto N6-based culture medium containing 3 mg/l of the selective agent bialaphos. Embryos, and later callus, are transferred to fresh selection plates every 2 weeks. After the first 14 days post-bombardment, the calli developing from the immature embryos are screened for GFP expression using an epifluorescent dissecting-microscope. Typically, (i.e. in the absence of a cell cycle gene) this is too early to observe growing multicellular transformants. Instead, as typical after such a short post-bombardment duration, numerous GFP-expressing single-cells are observed on control embryos (where the UBI::PAT~GFP::pinII plasmid is introduced alone), but GFP-expressing multicellular clusters are not observed. It is expected that when UBI::CycE::pinII is included along with the UBI::PAT~GFP::pinII marker, numerous GFP+ multicellular clusters are observed growing from the immature embryos at this same early time-point (14 days post-bombardment). The higher number of rapidly-growing transformants suggests that expression of CycE increases integration frequencies (thus higher numbers) and stimulates growth of these colonies after integration has occurred (thus, the transformants are clearly visible at this early juncture).

After 6–8 weeks, transformed calli are recovered. In treatments where both the PAT~GFP gene and CycE are transformed into immature embryos, a higher number of growing calli are expected on the selective medium and callus growth is stimulated (relative to treatments with the PAT-GFP gene alone).

Differences in cell cycle profiles are expected in CycE-expressing cells relative to control (wild-type) cells. To demonstrate that over-expression of CycE genes could accelerate cell division, the cell cycle profile of maize calli expressing Ubi::CycE are analyzed using a cell sorter (flow cytometry assay). Flow cytometry is a standard method to study cell cycle, using procedures that are well established in the literature, as, for example, in Sonea I M et al., Am J Vet Res. 1999 60(3):346–53.

Briefly, by counting the number of cells that are in G1 phase versus the number of cells that are in G2 phase, one can estimate, in a given population, the percentage of cells that are undergoing cell division. The higher the percentage of cells in G1 phase, the less the number of cells that are dividing. Under standard culture conditions, approximately 70% of the G1/G2 cells of maize calli are in the G1 phase. In maize calli expressing CycE genes, alterations of the distribution of cells in the G1 and G2 phases is expected. The frequency of cells in G1 declines, and the proportion of the cell population in either S or G2 phase increases (indicative of stimulating the progression from G1 into S phase in CycE-expressing cells). In control calli expressing similar vector genes but lacking a CycE gene, the cell cycle profile remains similar to that of the non-treated wild type maize calli.

Calli from the CycE treatment are expected to regenerate easily. Healthy, fertile transgenic plants are grown in the greenhouse. Seed-set on CycE transgenic plants is expected to be similar to control plants, and transgenic progeny are recovered.

It is expected that higher CycE-transgene expression levels improve transformation. For this bombardment experiment (to be performed in a similar manner to that described above), Hi-II ears are harvested at 10 DAP, and the immature embryos are divided evenly between the 3 treatments (125 embryos per treatment). The treatments include a no-cyclin control (UBI::PAT~GFP::pinII), or the UBI::PAT~GFP::pinII marker plus one of two cyclin-expressing plasmids (UBI::CycE or nos::CycE). For this experiment high levels of cyclin expression (UBI) are being compared to low levels (nos) of expression. When the UBI promoter drives expression, the transformation frequency for the CycE gene is expected to be increased. Placing the CycE gene behind the nos promoter is expected to produce a transformation frequency more similar to the control. It is expected that higher expression levels result in correspondingly higher recovery of transformants.

It is expected that increased maize transformation frequency can be affected by either increased transient activity of CycE (for example, where the selectable marker, UBI::PAT-GFP::pinII, and other genes of interest integrate into the genome and are subsequently expressed—but where CycE does not integrate), or co-integration of the functional CycE expression cassette along with the selectable marker and agronomic gene(s). Stable co-integration of CycE and PAT~GFP is described above in this example, and increasing transient activity is exemplified below.

Increasing Transient Activity of CycE

In order to transiently express CycE, it may be desirable to reduce the likelihood of ectopic stable expression of the CycE gene. Strategies for transient-only expression can be used. One such method is to express a recombinase, such as FLP, and flank the CycE expression cassette with an identical recombinase-target-sequence, such as the FRT sequence. Under these conditions, FLP recombinase activity will reduce stable integration of the FRT-flanked CycE cassette, thus limiting CycE expression to a transient interval.

Other strategies to transiently increase CycE activity include methods such as delivery of RNA (transcribed from the CycE gene) or CycE protein along with the transgene cassettes to be integrated to enhance transgene integration by transient stimulation of cell division. Using well-established methods to produce CycE-RNA, this can then be purified and introduced into maize cells using physical methods such as microinjection, bombardment, electroporation or silica fiber methods. For protein delivery, the gene is first expressed in a bacterial or baculoviral system, the protein purified and then introduced into maize cells using physical methods such as microinjection, bombardment, electroporation or silica fiber methods.

Alternatively, CycE proteins are delivered from *Argrobacterium tumefaciens* into plant cells in the form of fusions to *Argrobacterium* virulence proteins. Fusions are constructed between CycE and bacterial virulence proteins such as VirE2, VirD2, or VirF which are known to be delivered directly into plant cells. Fusions are constructed to retain both those properties of bacterial virulence proteins required to mediate delivery into plant cells and the CycE activity required for enhancing transgene integration. This method should ensure a high frequency of simultaneous co-delivery of T-DNA and functional CycE protein into the same host cell. The methods above represent various means of using the CycE gene, CycE-RNA or its encoded product to increase transformation frequency.

Example 5

Using the CycE Gene to Improve Soybean Transformation

Delivery of the GmCycE gene can be accomplished through numerous well-established methods for plant cells, including for example particle bombardment, sonication, PEG treatment or electroporation of protoplasts, electroporation of intact tissue, silica-fiber methods, microinjection or Agrobacterium-mediated transformation. Using one of the above methods, DNA is introduced into soybean cells capable of growth on suitable soybean maize culture medium. The CycE gene (GmCycE) is cloned into a cassette with a constitutive promoter (for example, the SCP-1 promoter which confers constitutive expression in soybean, see PHI Patent application WO 99/43838) and a 3' sequence such as the nos 3' region. Particle bombardment is used to introduce the SCP1::GmCycE::nos-containing plasmid along with a SCP1::HYG:nos-containing plasmid (which, when expressed produces a protein which confers hygromycin resistance) into soybean cells capable of growth on suitable soybean culture medium. Such competent cells can be from soybean suspension culture, cell culture on solid medium, freshly isolated cotyledonary nodes or meristem cells. Suspension-cultured somatic embryos of Jack, a Glycine max (I.) Merrill cultivar, are used as the target for co-delivery of a CycE and a HYG-expressing plasmid. For target tissues receiving the CycE expression cassette, transformation frequency is improved. Media for induction of cell cultures with high somatic embryogenic capacity, for establishing suspensions, and for maintenance and regeneration of somatic embryos are described in Bailey M A, Boerma H R, Parrott W A, 1993, Genotype effects on proliferative embryogenesis and plant regeneration of soybean, In Vitro Cell Dev Biol 29P:102–108. Likewise, methods for particle-mediated transformation of soybean are well established in the literature, see for example Stewart N C, Adang M J, All J N, Boerma H R, Cardineau G, Tucker D, Parrott W A, 1996, Genetic transformation, recovery and characterization of fertile soybean transgenic for a synthetic *Bacillus thuringiensis* crylAc gene, Plant Physiol 112:121–129.

Maintenance of Soybean Embryogenic Suspension Cultures

Soybean embryogenic suspension cultures are maintained in 35 ml liquid media SB196 or SB172 in 250 ml Erlenmeyer flasks on a rotary shaker, 150 rpm, 26C with cool white fluorescent lights on 16:8 hr day/night photoperiod at light intensity of 30–35 uE/m2s.

Cultures are subcultured every two weeks by inoculating approximately 35 mg of tissue into 35 ml of fresh liquid media. Alternatively, cultures are initiated and maintained in 6-well Costar plates.

SB 172 media is prepared as follows: (per liter), 1 bottle Murashige and Skoog Medium (Duchefa # M 0240), 1 ml B5 vitamins 1000× stock, 1 ml 2,4-D stock (Gibco 11215–019), 60 g sucrose, 2 g MES, 0.667 g L-Asparagine anhydrous (GibcoBRL 11013–026), pH 5.7.

SB 196 media is prepared as follows: (per liter) 10 ml MS FeEDTA, 10 ml MS Sulfate, 10 ml FN-Lite Halides, 10 ml FN-Lite P,B,Mo, 1 ml B5 vitamins 1000× stock, 1 ml 2,4-D, (Gibco 11215–019), 2.83 g KNO$_3$, 0.463 g (NH$_4$)$_2$SO$_4$, 2 g MES, 1 g Asparagine Anhydrous, Powder (Gibco 11013-026), 10 g Sucrose, pH 5.8.

2,4-D stock concentration 10 mg/ml is prepared as follows: 2,4-D is solubilized in 0.1 N NaOH, filter-sterilized, and stored at −20° C.

B5 vitamins 1000×stock is prepared as follows: (per 100 ml)—store aliquots at −20° C., 10 g myo-inositol, 100 mg nicotinic acid, 100 mg pyridoxine HCl, 1 g thiamine.

Particle Bombardment

Soybean embryogenic suspension cultures are transformed with various plasmids by the method of particle gun bombardment (Klein et al., 1987; Nature, 327:70.

To prepare tissue for bombardment, approximately two flasks of suspension culture tissue that has had approximately 1 to 2 weeks to recover since its most recent subculture is placed in a sterile 60×20 mm petri dish containing 1 sterile filter paper in the bottom to help absorb moisture. Tissue (i.e. suspension clusters approximately 3–5 mm in size) is spread evenly-across each petri plate. Residual liquid is removed from the tissue with a pipette, or allowed to evaporate to remove excess moisture prior to bombardment. Per experiment, 4–6 plates of tissue are bombarded. Each plate is made from two flasks.

To prepare gold particles for bombardment, 30 mg gold is washed in ethanol, centrifuged and resuspended in 0.5 ml of sterile water. For each plasmid combination (treatments) to be used for bombardment, a separate micro-centrifuge tube is prepared, starting with 50 µl of the gold particles prepared above. Into each tube, the following are also added; 5 µl of plasmid DNA (at 1 µg/µl), 50 µl CaCl$_2$, and 20 µl 0.1 M spermidine. This mixture is agitated on a vortex shaker for 3 minutes, and then centrifuged using a microcentrifuge set at 14,000 RPM for 10 seconds. The supernatant is decanted and the gold particles with attached, precipitated DNA are washed twice with 400 µl aliquots of ethanol (with a brief centrifugation as above between each washing). The final volume of 100% ethanol per each tube is adjusted to 40 µl, and this particle/DNA suspension is kept on ice until being used for bombardment.

Immediately before applying the particle/DNA suspension, the tube is briefly dipped into a sonicator bath to disperse the particles, and then 5 UL of DNA prep is pipetted onto each flying disk and allowed to dry. The flying disk is then placed into the Dupont Biolistics PDS1000/HE. Using the DuPont Biolistic PDS1000/HE instrument for particle-mediated DNA delivery into soybean suspension clusters, the following settings are used. The membrane rupture pressure is 1100 psi. The chamber is evacuated to a vacuum of 27–28 inches of mercury. The tissue is placed approximately 3.5 inches from the retaining/stopping screen (3rd shelf from the bottom). Each plate is bombarded twice, and the tissue clusters are rearranged using a sterile spatula between shots.

Following bombardment, the tissue is re-suspended in liquid culture medium, each plate being divided between 2 flasks with fresh SB196 or SB172 media and cultured as described above. Four to seven days post-bombardment, the medium is replaced with fresh medium containing 25 mg/L hygromycin (selection media). The selection media is refreshed weekly for 4 weeks and once again at 6 weeks. Weekly replacement after 4 weeks may be necessary if cell density and media turbidity is high.

Four to eight weeks post-bombardment, green, transformed tissue may be observed growing from untransformed, necrotic embryogenic clusters. Isolated, green tissue is removed and inoculated into 6-well microtiter plates with liquid medium to generate clonally-propagated, transformed embryogenic suspension cultures.

Each embryogenic cluster is placed into one well of a Costar 6-well plate with 5 mls fresh SB196 media with 25 mg/L hygromycin. Cultures are maintained for 2–6 weeks with fresh media changes every 2 weeks. When enough tissue is available, a portion of surviving transformed clones are subcultured to a second 6-well plate as a back-up to protect against contamination.

In treatments where both the HYG and CycE expression cassettes are transformed into immature embryos, a higher number of growing embryogenic cultures are expected on the selective medium and growth of embryogenic cultures is stimulated (relative to treatments with the HYG gene alone).

Regeneration of Soybean Somatic Embryos

To promote in vitro maturation, transformed embryogenic clusters are removed from liquid SB196 and placed on solid agar media, SB 166, for 2 weeks. Tissue clumps of 2–4 mm size are plated at a tissue density of 10 to 15 clusters per plate. Plates are incubated in diffuse, low light (<10 $\mu$E) at 26+/−1° C. After two weeks, clusters are subcultured to SB 103 media for 3–4 weeks.

SB 166 is prepared as follows: (per liter), 1 pkg. MS salts (Gibco/ BRL-Cat # 11117-017), 1 ml B5 vitamins 1000× stock, 60 g maltose, 750 mg MgCl2 hexahydrate, 5 g activated charcoal, pH 5.7, 2 g gelrite.

SB 103 media is prepared as follows: (per liter), 1 pkg. MS salts (Gibco/BRL-Cat# 11117-017), 1 ml B5 vitamins 1000× stock, 60 g maltose, 750 mg MgCl2 hexahydrate, pH 5.7, 2 g gelrite.

After 5–6 week maturation, individual embryos are desiccated by placing embryos into a 100×15 petri dish with a 1 cm2 portion of the SB103 media to create a chamber with enough humidity to promote partial desiccation, but not death.

Approximately 25 embryos are desiccated per plate. Plates are sealed with several layers of parafilm and again are placed in a lower light condition. The duration of the desiccation step is best determined empirically, and depends on size and quantity of embryos placed per plate. For example, small embryos or few embryos/plate require a shorter drying period, while large embryos or many embryos/plate require a longer drying period. It is best to check on the embryos after about 3 days, but proper desiccation will most likely take 5 to 7 days. Embryos will decrease in size during this process.

Desiccated embryos are planted in SB 71-1 or MSO medium where they are left to germinate under the same culture conditions described for the suspension cultures. When the plantlets have two fully-expanded trifoliolate leaves, germinated and rooted embryos are transferred to sterile soil and watered with MS fertilizer. Plants are grown to maturity for seed collection and analysis. Embryogenic cultures from the CycE treatment are expected to regenerate easily. Healthy, fertile transgenic plants are grown in the greenhouse. Seed-set on CycE transgenic plants is expected to be similar to control plants, and transgenic progeny are recovered.

SB 71-1 is prepared as follows: 1 bottle Gamborg's B5 salts w/sucrose (Gibco/BRL-Cat# 21153–036), 10 g sucrose, 750 mg MgCl2 hexahydrate, pH 5.7, 2 g gelrite.

MSO media is prepared as follows: 1 pkg Murashige and Skoog salts (Gibco 11117-066), 1 ml B5 vitamins 1000× stock, 30 g sucrose, pH 5.8, 2 g Gelrite.

It is expected that higher CycE-transgene expression levels improve transformation. For this bombardment experiment (to be performed in a similar manner to that described above), soybean suspension cultures are used as the target tissue for bombardment. The treatments include a no-cyclin control (SCP1::HYG::nos), or the SCP1::HYG::nos marker plus one of two cyclin-expressing plasmids (SCP1::CycE::nos or nos::CycE::nos). For this experiment high levels of cyclin expression (SCP1) are compared to low levels (nos) of expression. When the SCP1 promoter drives expression, the transformation frequencies for the CycE genes are expected to be increased. Placing the CycE gene behind the nos promoter is expected to produce a transformation frequency more similar to the control. It is expected that higher expression levels result in correspondingly higher recovery of transformants.

Example 6

Identifying Transformants in the Absence of Chemical Selection

When the CycE gene is introduced without any additional selective marker, transgenic calli can be identified by their ability to grow more rapidly than surrounding wild-type (non-transformed) tissues. This differential growth advantage can be used to identify CycE-transgenic calli in the absence of conventional chemical selection (i.e. based solely on increased growth rates relative to the growth of non-transgenic callus). Transgenic callus can be verified using PCR and Southern analysis. Northern analysis can also be used to verify which calli are expressing the bar gene, and which are expressing the maize CycE gene at levels above normal wild-type cells (based on hybridization of probes to freshly isolated mRNA population from the cells).

Inducible Expression

The CycE gene can also be cloned into a cassette with an inducible promoter such as the benzenesulfonamide-inducible promoter. The expression vector is co-introduced into plant cells and after selection on bialaphos, the transformed cells are exposed to the safener (inducer). Increased growth of CycE-transgenic callus can be observed after the application of the safener induction. The cells are screened for the presence of CycE RNA by northern, or RT-PCR (using transgene specific probes/oligo pairs), for CycE-encoded protein using CycE-specific antibodies in Westerns or using hybridization. Cell cycle assays could also be employed, as described above.

Example 7

Control of CycE Gene Expression Using Tissue-specific or Cell-specific Promoters Provides a Differential Growth Advantage CycE gene expression using tissue-specific or cell-specific promoters stimulates cell cycle progression in the expressing tissues or cells. For example, using a seed-specific promoter will stimulate the cell division rate and result in increased seed biomass. Alternatively, driving CycE expression with a strongly-expressed, early, tassel-specific promoter will enhance development of this entire reproductive structure.

Expression of CycE genes in other cell types and/or at different stages of development will similarly stimulate cell division rates. Similar to results observed in Arabidopsis (Doerner et al., 1996), root-specific or root-preferred expression of CycE will result in larger roots and faster growth (i.e. more biomass accumulation).

Example 8

Meristem Transformation

Meristem transformation protocols rely on the transformation of apical initials or cells that can become apical initials following reorganization due to injury or selective pressure. The progenitors of these apical initials differentiate to form the tissues and organs of the mature plant (i.e. leaves, stems, ears, tassels, etc.). The meristems of most angiosperms are layered with each layer having its own set of initials. Normally in the shoot apex these layers rarely mix. In maize the outer layer of the apical meristem, the L1, differentiates to form the epidermis while descendents of cells in the inner layer, the L2, give rise to internal plant parts including the gametes. The initials in each of these layers are defined solely by position and can be replaced by adjacent cells if they are killed or compromised. Meristem transformation frequently targets a subset of the population of apical initials and the resulting plants are chimeric. If for example, 1 of 4 initials in the L1 layer of the meristem are transformed only ¼ of epidermis would be transformed.

Selective pressure can be used to enlarge sectors but this selection must be non-lethal since large groups of cells are required for meristem function and survival. Transformation of an apical initial with a CycE expression cassette under the expression of a promoter active in the apical meristem (either meristem specific or constitutive) would allow the transformed cells to grow faster and displace wildtype initials driving the meristem towards homogeneity and minimizing the chimeric nature of the plant body. To demonstrate this, the CycE gene is cloned into a cassette with a promoter that is active within the meristem (i.e. either a strong constitutive maize promoter such as the ubiquitin promoter including the first ubiquitin intron, or a promoter active in meristematic cells such as the maize histone, cdc2 or actin promoter). Coleoptilar stage embryos are isolated and plated meristem up on a high sucrose maturation medium (see Lowe et al., 1997). The cyclin D expression cassette along with a reporter construct such as Ubi:GUS:pinII can then be co-delivered (preferably 24 hours after isolation) into the exposed apical dome using conventional particle gun transformation protocols. As a control the CycE construct can be replaced with an equivalent amount of pUC plasmid DNA. After a week to 10 days of culture on maturation medium the embryos can be transferred to a low sucrose hormone-free germination medium. Leaves from developing plants can be sacrificed for GUS staining. Transient expression of the CycE gene in meristem cells, through stimulation of the G1→S transition, will result in greater integration frequencies and hence more numerous transgenic sectors. Integration and expression of the CycE gene will impart a competitive advantage to expressing cells resulting in a progressive enlargement of the transgenic sector. Due to the enhanced growth rate in CycE-expressing meristem cells, they will supplant wild-type meristem cells as the plant continues to grow. The result will be both enlargement of transgenic sectors within a given cell layer (i.e. periclinal expansion) and into adjacent cell layers (i.e. anticlinal invasions). As an increasingly large proportion of the meristem is occupied by CycE-expressing cells, the frequency of CycE germline inheritance should go up accordingly.

Example 9

Use of Flp/Frt System to Excise the CycE Cassette

In cases where the CycE gene has been integrated and CycE expression is useful in the recovery of maize trangenics, but is ultimately not desired in the final product, the CycE expression cassette (or any portion thereof that is flanked by appropriate FRT recombination sequences) can be excised using FLP-mediated recombination (see U.S. Pat. No. 5,929,301). In cases where transient CycE expression is desired, FLP recombinase activity concomitant with introduction of an FRT-flanked CycE expression cassette will reduce the incidence of stable CycE integration, thus confining CycE expression and activity to a transient interval. Variations on the wild-type yeast FRT sequence having utility for such applications as the uses described here can be found in PHI patent application WO 09/193502.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated ribonucleic acid sequence encoding a protein having SEQ ID NO: 2.

2. An isolated nucleic acid encoding a protein having Cyclin E activity, wherein the nucleic acid comprises a polynucleotide that encodes a polypeptide of SEQ ID NO: 2.

3. An isolated nucleic acid that modulates the level of Cyclin E protein in a cell when compared to a corresponding cell that does not contain the isolated nucleic acid, wherein the nucleic acid comprises a polynucleotide having the sequence set forth in SEQ ID NO: 1.

4. An isolated nucleic acid that modulates the level of Cyclin E protein in a cell when compared to the level of Cyclin E in a corresponding cell that does not contain the isolated nucleic acid, wherein the nucleic acid comprises a polynuoleotide fully complementary to the sequence set forth in SEQ ID NO: 1.

* * * * *